(12) United States Patent
Horiuchi et al.

(10) Patent No.: US 8,569,751 B2
(45) Date of Patent: Oct. 29, 2013

(54) HETEROCYCLIC COMPOUND AND ORGANIC LIGHT-EMITTING DEVICE USING THE SAME

(75) Inventors: Takayuki Horiuchi, Tokyo (JP); Jun Kamatani, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 7 days.

(21) Appl. No.: 13/390,681

(22) PCT Filed: Aug. 4, 2010

(86) PCT No.: PCT/JP2010/063596
§ 371 (c)(1),
(2), (4) Date: Feb. 15, 2012

(87) PCT Pub. No.: WO2011/021545
PCT Pub. Date: Feb. 24, 2011

(65) Prior Publication Data
US 2012/0153269 A1    Jun. 21, 2012

(30) Foreign Application Priority Data
Aug. 20, 2009 (JP) ................ 2009-190634

(51) Int. Cl.
*H01L 27/32* (2006.01)
(52) U.S. Cl.
USPC .................................................. 257/40
(58) Field of Classification Search
USPC .................. 257/40, E51.026, E27.119
See application file for complete search history.

(56) References Cited

U.S. PATENT DOCUMENTS

| | | | |
|---|---|---|---|
| 2008/0012475 A1* | 1/2008 | Oyamada et al. | 313/504 |
| 2008/0122344 A1 | 5/2008 | Shin | |
| 2009/0160327 A1* | 6/2009 | Oda et al. | 313/504 |
| 2011/0049479 A1* | 3/2011 | Yamada et al. | 257/40 |
| 2011/0180790 A1* | 7/2011 | Nakano et al. | 257/40 |
| 2011/0220883 A1* | 9/2011 | Nakano et al. | 257/40 |

FOREIGN PATENT DOCUMENTS

| | | |
|---|---|---|
| JP | 10-189247 A | 7/1998 |
| JP | 2005-235787 A | 9/2005 |
| JP | 2009-132627 A | 6/2009 |
| JP | 2010-111635 A | 5/2010 |
| WO | 2008-015945 A1 | 2/2008 |
| WO | 2008-059713 A1 | 5/2008 |

OTHER PUBLICATIONS

Yamada et al., Nitrogen-substitution effects on the mutagenicity and cytochrome P450 isofomn-selectivity of chrysene analog, Mutation Research, 2005, 586, 87-95.

Lewanowicz et al., Electronic spectra and luminescence properties of 4,10-diazachrysene in crystalline and glassy matrices at 77 K, Acta Physica Polonica, 1978, vol. A53, No. 2, p. 263-280.

Demeter et al., Dual luminescence properties of differently benzo-fused N-phenylphenanthridinones, Photochemical Photbiological Sciences, 2003,vol. 2, No. 3, p. 273-281.

* cited by examiner

*Primary Examiner* — Thao Le
(74) *Attorney, Agent, or Firm* — Canon U.S.A., Inc., IP Division

(57) ABSTRACT

An organic light-emitting device includes an anode, a cathode, and an organic compound layer interposed between the anode and the cathode. The organic compound layer contains a heterocyclic compound having 4,10-Diazachrysene.

2 Claims, 1 Drawing Sheet

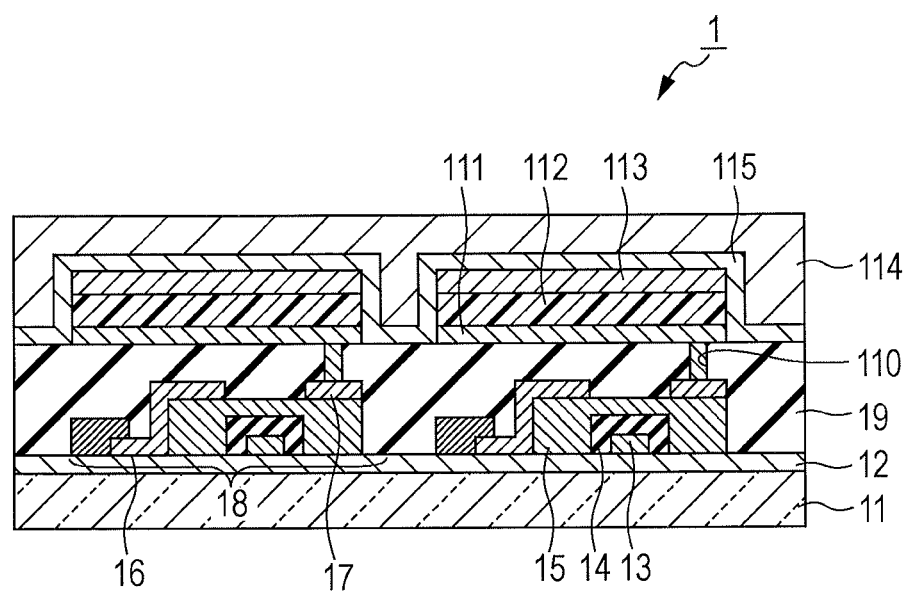

HETEROCYCLIC COMPOUND AND ORGANIC LIGHT-EMITTING DEVICE USING THE SAME

TECHNICAL FIELD

The present invention relates to a heterocyclic compound and an organic light-emitting device using the heterocyclic compound.

BACKGROUND ART

Organic light-emitting devices are a type of light-emitting device that includes a thin film containing a fluorescent organic compound interposed between an anode and a cathode. When electrons and holes are injected from the respective electrodes, excitons of the fluorescent compound are generated and the organic light-emitting device emits light as the excitons return to their ground state.

The recent advancement of organic light-emitting devices has been remarkable. Organic light-emitting devices have made it possible to produce thin and light-weight light-emitting devices that have high luminance at a low application voltage and a wide variety of emission wavelengths and display rapid response. This suggests that the organic light-emitting devices can be used in a wide variety of usages.

However, presently, there remains room for improvements. To be more specific, emitted light needs to have a higher luminance and the optical conversion efficiency needs to be increased for practical applications. Moreover, improvements are needed in terms of durability, such as changes with time caused by long use and deterioration caused by oxygen-containing atmospheric gas and humidity. In order for organic light-emitting devices to be used in full color displays and the like, one of the characteristics required of the organic light-emitting devices is that blue light is emitted at a high color purity and high efficiency. However, this has not been satisfactorily achieved. Accordingly, organic light-emitting devices that exhibit high color purity, emission efficiency, and durability and the materials that can be used to make such devices are in demand.

Various compounds and organic light-emitting devices using the compounds have been proposed to address the challenges described above. For example, PTL 1 to PTL 4 propose organic compounds having fluoranthene and benzofluoranthene backbones and organic light-emitting devices that use such organic compounds. However, their emission hue, emission efficiency, luminance, and durability need to be improved further.

NPL 1 proposes an organic compound having a 4,10-diazachrysene backbone and a synthetic method therefor.
Citation List
Patent Literature
   PTL 1 Japanese Patent Laid-Open No. 10-189247
   PTL 2 Japanese Patent Laid-Open No. 2005-235787
   PTL 3 International Publication 2008/015945
   PTL 4 International Publication 2008/059713
Non Patent Literature
   NPL 1 Mutation Research, 586, 87-95 (2005)

SUMMARY OF INVENTION

An aspect of the present invention provides a heterocyclic compound represented by general formula [1] below.

[Chem. 1]

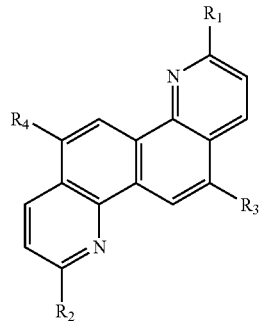

[1]

In formula [1], $R_1$ to $R_4$ each independently represent a hydrogen atom, a substituted or unsubstituted aryl group, or a substituted or unsubstituted heterocyclic group; and at least one of $R_1$ to $R_4$ represents a substituted or unsubstituted fused polycyclic aromatic group having four or more rings or a substituted or unsubstituted fused polycyclic heterocyclic group having four or more rings.

BRIEF DESCRIPTION OF DRAWINGS

FIG. 1 is a cross-sectional view of an example of an image display apparatus equipped with an organic light-emitting device according to one embodiment of the present invention.

DESCRIPTION OF EMBODIMENTS

A heterocyclic compound according to an embodiment of the present invention is first described. The organic compound of this embodiment is represented by general formula [1] below.

[Chem. 2]

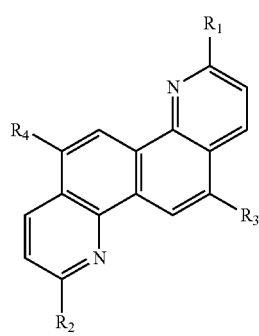

[1]

In formula [1], $R_1$ to $R_4$ each independently represent a hydrogen atom, a substituted or unsubstituted aryl group, or a substituted or unsubstituted heterocyclic group.

Examples of the aryl group represented by $R_1$ to $R_4$ include, but are not limited to, a phenyl group, a naphthyl group, an indenyl group, a biphenyl group, and a terphenyl group. Fused polycyclic aromatic groups having four or more rings described below are also included in this aryl group.

Examples of the heterocyclic group represented by $R_1$ to $R_4$ include, but are not limited to, a pyridyl group, a quinolyl group, an oxazolyl group, an oxadiazolyl group, a thiazolyl group, a thiadiazolyl group, a carbazolyl group, an acridinyl group, and a phenanthrolyl group. Fused polycyclic heterocyclic groups having four or more rings described below are also included in this heterocyclic group.

Examples of the substituents that may be contained in the aryl group and the heterocyclic group described above include, but are not limited to, alkyl groups such as a methyl group, an ethyl group, a propyl group, and a tertiary butyl group, aralkyl groups such as a benzyl group, aryl groups such as a phenyl group, a 3,5-di-(tert-butyl)phenyl group, and a biphenyl group, heterocyclic groups such as a pyridyl group and a pyrrolyl group, substituted amino groups such as a dimethylamino group, a diethylamino group, a dibenzylamino group, a diphenylamino group, and a ditolylamino group, alkoxy groups such as a methoxy group, an ethoxy group, and a propoxy group, aryloxy groups such as a phenoxyl group, halogen atoms such as fluorine, chlorine, bromine, and iodine atoms, and a cyano group.

In this embodiment, at least one of $R_1$ to $R_4$ represents substituted or unsubstituted fused polycyclic aromatic group having four or more rings or a substituted or unsubstituted fused polycyclic heterocyclic group having four or more rings.

Examples of the fused polycyclic aromatic group having four or more rings include, but are not limited to, a chrysenyl group, a pyrenyl group, a fluoranthenyl group, a benzo[k]fluoranthenyl group, a benzo[b]fluoranthenyl group, and a perylenyl group. Among the fused polycyclic aromatic groups having four or more rings described above, a benzo[k]fluoranthenyl group can be used due to its high fluorescent quantum yield.

Examples of the fused polycyclic heterocyclic group having four or more rings include, but are not limited to, an azachrysenyl group, an azapyrenyl group, an azafluoranthenyl group, an azabenzo[k]fluoranthenyl group, an azabenzo[b]fluoranthenyl group, and an azaperylenyl group.

Specific examples of the substituent that may be contained in the fused polycyclic aromatic group or the fused polycyclic heterocyclic group are the same as those substituents that may be contained in the aryl group or the heterocyclic group described above.

The requirements for the constituent material of an organic light-emitting device are that sublimation purification can be utilized as a purification method for increasing the purity of the material and that vacuum vapor deposition can be utilized to form organic compound layers. In conducting sublimation and vacuum deposition, the constituent material of the organic light-emitting device is exposed to a temperature of 300 degrees Celsius or higher in high vacuum of about $10^{-3}$ Pa. When the molecular weight of the constituent material of the organic light-emitting device is more than 1000, the material itself is exposed to a higher temperature condition. As a result, the material may be thermally decomposed and desired physical properties may no longer be obtained. Thus, the heterocyclic compound of this embodiment used as a constituent material of an organic light-emitting device may have a molecular weight of 1000 or less.

The characteristics of the heterocyclic compound of this embodiment will now be described. The heterocyclic compound of this embodiment is a compound having a 4,10-diazachrysene backbone, i.e., a chrysene having the 4-position carbon and the 10-position carbon substituted by nitrogen, as the basic structure. Carbon atoms at the 3-position and the 9-position of 4,10-diazachrysene (corresponding to $R_1$ and $R_2$ in formula [1]) are bonded to nitrogen atoms which have an electronegativity higher than that of carbon atoms. Thus, the carbon atoms at the 3-position and the 9-position are more positively charged than other carbon atoms in the backbone. When hydrogen atoms are bonded to the carbon atoms at the 3-position and 9-position carbon atoms, these hydrogen atoms may dissociate by forming $H^+$ (protons), possibly resulting in decomposition of the compound itself. In contrast, the carbon atoms at the 6-position and the 12-position have a high electron density and their reactivity to electrophilic reactions is highest. Thus, when hydrogen atoms are bonded to the carbon atoms at the 6-position and the 12-position (i.e., when no substituent is introduced), the compound may become decomposed by the electrophilic reaction (oxidation reaction) with singlet molecular oxygen and the like.

Thus, the heterocyclic compound of this embodiment needs to have a substituent introduced into the 3-, 6-, 9- or 12-position of the 4,10-diazachrysene backbone, i.e., the basic structure. However, when a substituent having methylene, such as an alkyl group, is introduced, the methylene contributes to the above-mentioned electrophilic substitution reaction, which is not favorable. Accordingly, an aryl group or a heterocyclic group which is a substituent having no methylene and including $sp_2$ carbon atoms may be introduced to the 3-, 6-, 9- or 12-position of the 4,10-diazachrysene backbone.

When the heterocyclic compound of this embodiment is used as a constituent material of a blue light-emitting device, the emission peak of the material itself must be in the range of 430 nm to 480 nm. Examples of the fused polycyclic compound that generates blue fluorescence include fused polycyclic aromatic compounds having four or more rings. In particular, fluoranthene, benzo[k]fluoranthene, benzo[b]fluoranthene, and the like are available. Heterocyclic compounds having some of carbon atoms in the fused polycyclic compounds substituted by nitrogen atoms have substantially the same fluorescent color. However, the optical absorption wavelength required to generate the lowest electronically excited singlet state of the fused polycyclic compound described above is short, as indicated in Table 1 below.

TABLE 1

| | Absorption |
|---|---|
| Fluoranthene | 366 nm* |
| Benzo[k]fluoranthene | 378 nm* |
| Benzo[b]fluoranthene | 358 nm* |

*The optical absorption wavelength was calculated in accordance with molecular orbital study (density functional theory, B3LYP/6-31G* level).

In this embodiment, a fused polycyclic aromatic group or fused polycyclic heterocyclic group that displays short-wavelength (blue) fluorescence is introduced into one of the 3-, 6-, 9-, and 12-positions of the basic structure, 4,10-diazachrysene. In particular, a fused polycyclic aromatic group or fused polycyclic heterocyclic group that displays short wavelength (blue) fluorescence is introduced into one of $R_1$ to $R_4$ in formula [1]. A fused polycyclic aromatic group or fused polycyclic heterocyclic group that has four or more rings (four or more rings and eight or less rings) can be introduced. As a result, the pi conjugate plane of the entire molecule is expanded and the lowest excited singlet energy is lowered, thereby increasing the optical absorption wavelength necessary for creating the lowest excited singlet state. The heterocyclic compound of this embodiment in a diluted solution thus has an emission peak at 430 nm to 450 nm, which is within the suitable range for blue emission (430 nm to 480 nm). The fused polycyclic aromatic group or fused polycyclic heterocyclic group having four or more rings to be introduced into one of the 3-, 6-, 9-, and 12-positions of the 4,10-diazachrysene backbone can be a fluoranthenyl group, a benzo[k]fluoranthenyl group, or a benzo[b]fluoranthenyl group. This is because these substituents have low reactivity to electrophilic reactions due to the electron-withdrawing effect of the five-membered-ring structure, and are thus chemically stable. Among these substituents, the benzo[k]fluoranthenyl group having a high quantum yield is particularly suitable.

When a fused polycyclic aromatic group or a fused polycyclic heterocyclic group is introduced into the 4,10-diazachrysene basic structure, the molecular weight of the compound itself is increased. In particular, the molecular weight of the compound increases to 400 or more. When the molecular weight of the compound itself is large, phenomena that occurs when the molecular amount of the compound itself is small, namely, phenomena such as concentration quenching caused by cohesion of the compound, the increase in emission wavelength, crystallization, and instability of the vapor deposition rate, rarely occur. Thus, when the heterocyclic compound of this embodiment is used as a constituent material of an organic light-emitting device, cohesion can be suppressed, thin film stability can be enhanced, and the vapor deposition stability can be improved.

The heterocyclic compound of this embodiment has an electron injection property since nitrogen atoms contained therein are electrophilic. Thus, when the heterocyclic compound is used as a constituent material of an organic light-emitting device, the driving voltage of the device can be lowered. Since the heterocyclic compound of this embodiment has two nitrogen atoms in a molecule, the effect of lowering the driving voltage of the device is high compared to those compounds having backbones, such as pyridine and quinoline backbones, that have only one nitrogen atom.

Molecules that undergo charge-transfer (CT) emission may be sometimes formed depending on the HOMO and the LUMO levels of the substituent introduced into one of $R_1$ to $R_4$ of formula [1]. When molecules that undergo CT emission are generated, it is possible to adjust the original blue fluorescent property of the substituent introduced into one of $R_1$ to $R_4$ to a blue fluorescent property that suits a desired purpose. To be more specific, the following two cases are conceivable.

(1) The case where $HOMO_{substituent} > HOMO_{backbone}$ and $LUMO_{substituent} > LUMO_{backbone}$ and (2) the case where $HOMO_{substituent} < HOMO_{backbone}$ and $LUMO_{substituent} < LUMO_{backbone}$ (where $HOMO_{substituent}$ and $LUMO_{substituent}$ respectively represent a HOMO level and a LUMO level of a substituent introduced into one of $R_1$ to $R_4$ and $HOMO_{backbone}$ and $LUMO_{backbone}$ respectively represent a HOMO level and a LUMO level of 4,10-diazachrysene.)

In the case of (1), CT emission occurs between $HOMO_{substituent}$ and $LUMO_{backbone}$. In the case of (2), CT emission occurs between $HOMO_{backbone}$ and $LUMO_{substituent}$. In either cases, the molecular design is effective for increasing the wavelength of the fluorescence derived from the substituent introduced into one of $R_1$ to $R_4$.

Specific examples of the heterocyclic compound of this embodiment are shown below. However, the present invention is not limited to these examples.

[Chem. 3]

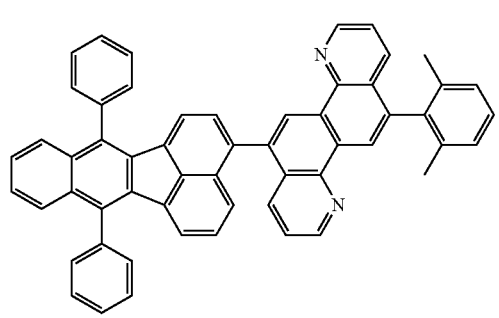

1-1

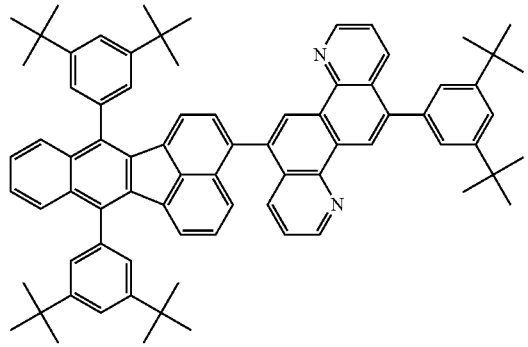

1-2

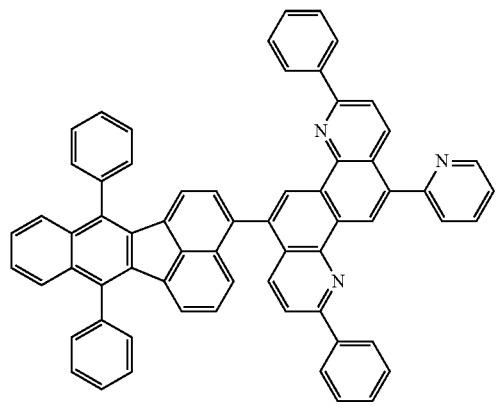

1-3

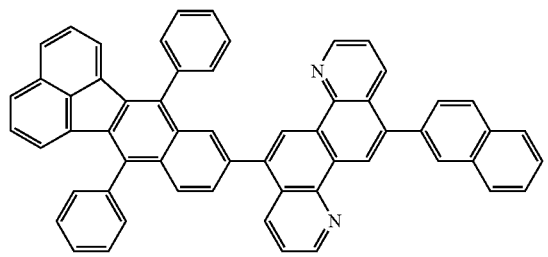

1-4

-continued
1-5
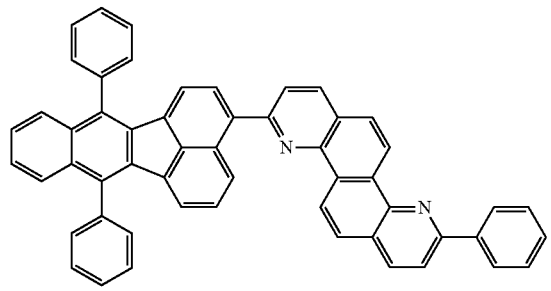
1-6
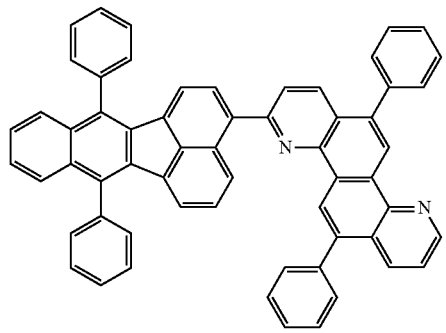
1-7
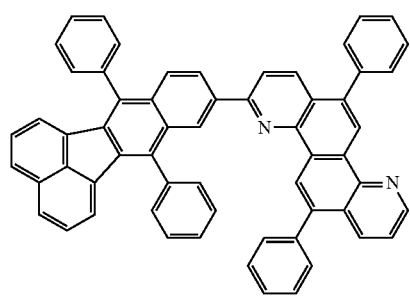
1-8
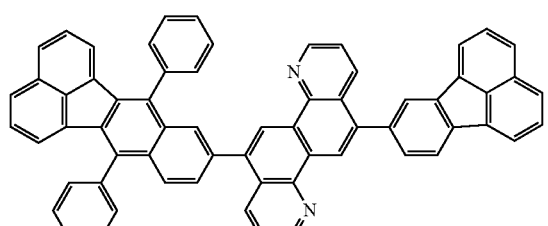
1-9
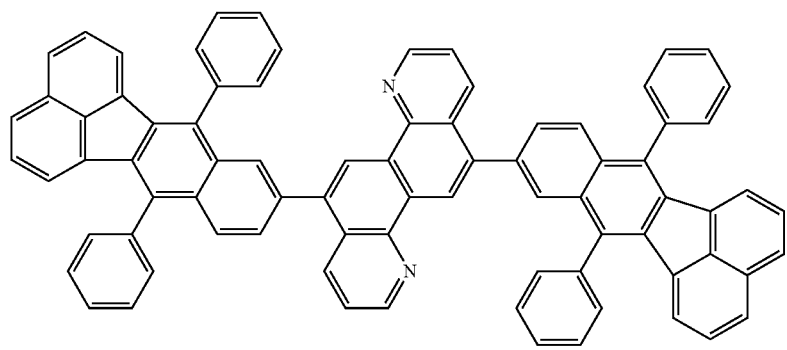
1-10
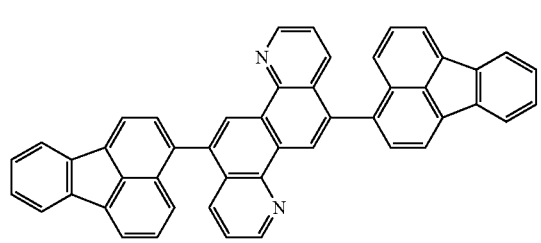
1-11
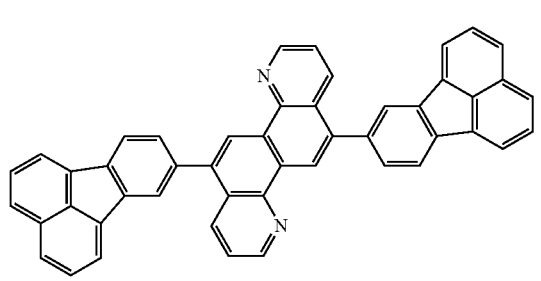
1-12
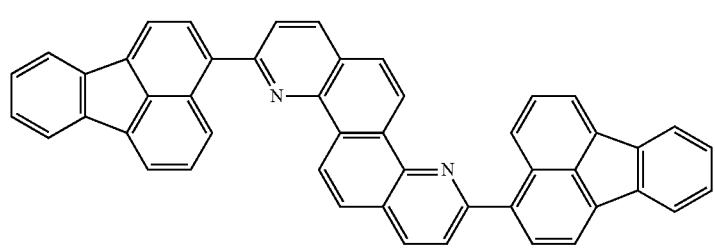

1-13

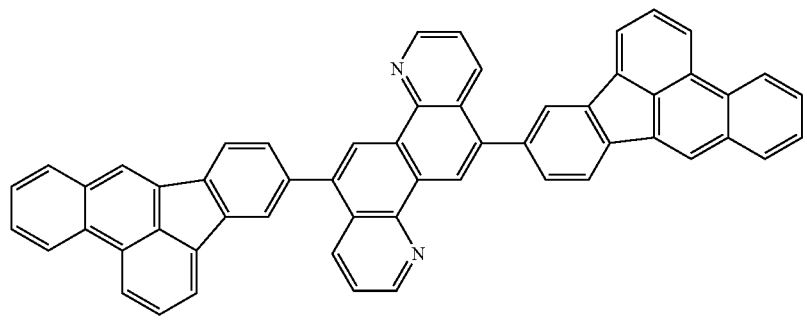

1-15

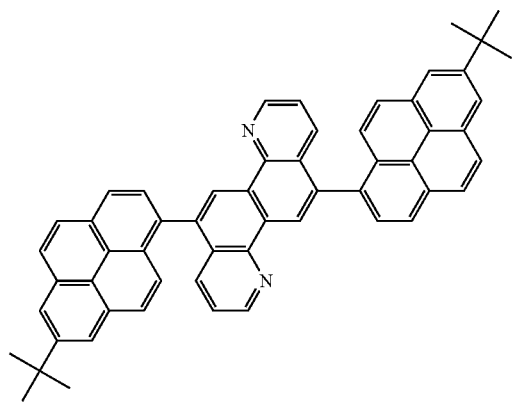

1-16

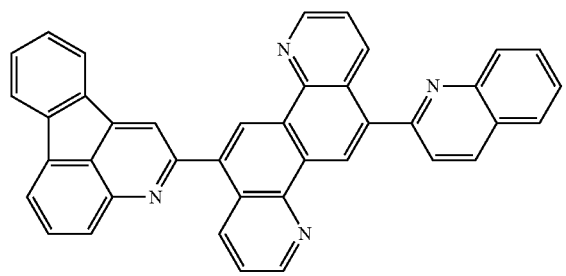

1-17

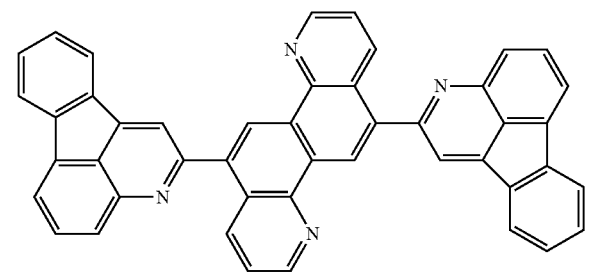

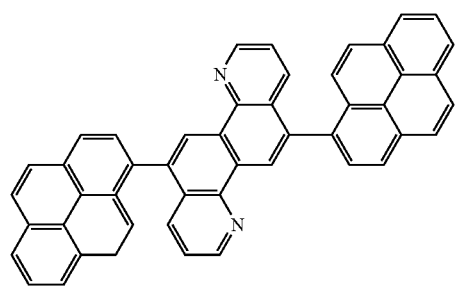

An organic light-emitting device according to an embodiment of the present invention will now be described.

The organic light-emitting device of this embodiment includes an anode, a cathode, and an organic compound layer interposed between the anode and the cathode. The organic compound layer of the organic light-emitting device contains the organic compound described above. The organic compound can be contained in an emission layer.

When the organic compound is contained in the emission layer, the emission layer may be composed of only the organic compound or may be constituted by a host and a guest.

When the emission layer is constituted by the host and the guest, the host is a material that has the largest weight ratio among the constituent materials of the emission layer, i.e., the material that serves as the main component. The guest is also referred to as "dopant" and is a material contained in the emission layer to serve as an auxiliary component together with an emission assist material, a charge injection material, etc. The organic compound may be used as the host or the guest. The organic compound is more suited to be used as the guest. When the organic compound is used as the guest, an organic light-emitting device that can output light at a high luminance and high efficiency and has significantly high durability can be obtained.

When the heterocyclic compound of this embodiment is used as the guest, the corresponding host is not particularly limited. However, fused polycyclic aromatic compounds described below can be used to form stable amorphous films. In order to provide an organic light-emitting device that has high efficiency and high durability, the emission yield of the host itself must be high and the host needs to be chemically stable. Thus, among the fused polycyclic aromatic compounds usable as the host, fused polycyclic aromatic compounds that have high fluorescent quantum yield and chemical stability can be used. Examples thereof include fluorene derivatives, pyrene derivatives, fluoranthene derivatives, and benzofluoranthene derivatives.

When the organic compound of the embodiment is used as the guest, the concentration of the guest relative to the host is preferably 0.01 wt % or more and 20 wt % or less and more preferably 0.5 wt % or more and 10 wt % or less.

Specific structural examples of the organic light-emitting device of this embodiment are described below. These specific examples are merely basic device configurations which do not limit the scope of the present invention.

(1) anode/emission layer/cathode
(2) anode/hole transport layer/electron transport layer/cathode
(3) anode/hole transport layer/emission layer/electron transport layer/cathode
(4) anode/hole injection layer/hole transport layer/emission layer/electron transport layer/cathode
(5) anode/hole transport layer/emission layer/hole-exciton blocking layer/electron transport layer/cathode Various structures other than the structures of (1) to (5) may be employed. For example, an insulating layer, an adhesive layer, or an interference layer may be formed at the interface between an electrode and an organic compound layer. For example, an electron transport layer or a hole transport layer may be constituted by two layers having different ionization potentials.

If needed, the organic light-emitting device can use any other available compound in addition to the organic compound of the embodiment. In particular, the following compounds can be used.

(a) low-molecular-weight and high-molecular-weight hole injection compounds and hole transport compounds
(b) host compounds that serve as the host of the emission layer
(c) light-emitting compounds
(d) electron injection compounds and electron transport compounds Examples of these compounds are described below.

The hole injection compound and the hole transport compound can be materials having high hole mobility. Examples of the low-molecular-weight and high-molecular-weight materials that have functions of injecting and transporting holes include, but are not limited to, triarylamine derivatives, phenylene diamine derivatives, stilbene derivatives, phthalocyanine derivatives, porphyrin derivatives, poly(vinylcarbazole), poly(thiophene), and other electrically conductive polymers. However, the present invention is not limited to these examples.

Examples of the host compound include compounds shown in Table 2 below. Derivatives of the compounds shown in Table 2 may also be used.

TABLE 2

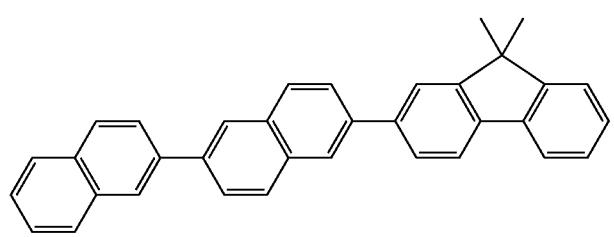 [SMILES: CC1(C)c2ccccc2-c2ccc(-c3ccc4cc(-c5ccc6ccccc6c5)ccc4c3)cc21]

H1

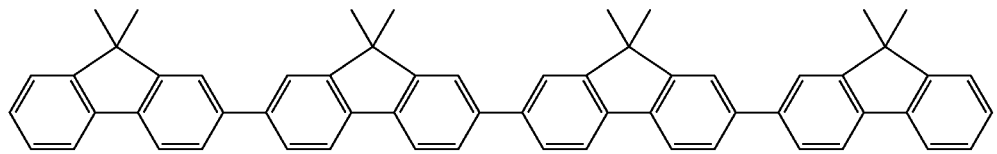 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]

H2

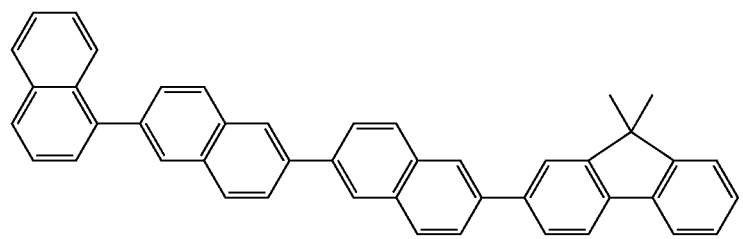 [SMILES: CC1(C)c2ccccc2-c2ccc(-c3ccc4cc(-c5ccc6cc(-c7cccc8ccccc78)ccc6c5)ccc4c3)cc21]

H3

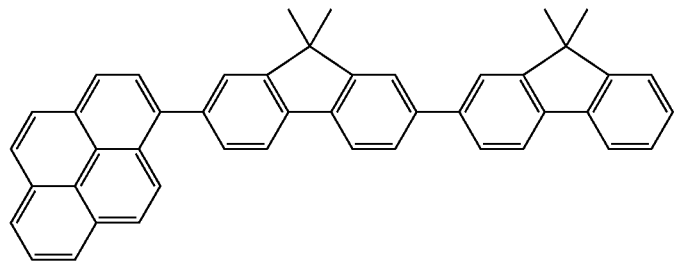 [SMILES: CC1(C)c2ccccc2-c2ccc(-c3ccc4c(c3)C(C)(C)c3cc(-c5ccc6ccc7cccc8ccc5c6c78)ccc3-4)cc21]

H4

TABLE 2-continued
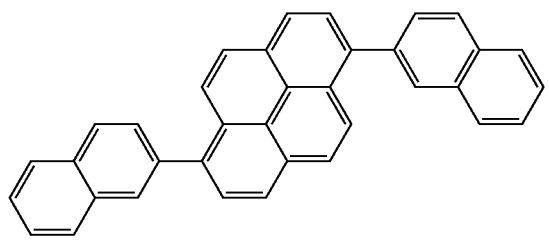 [SMILES: c1ccc2cc(-c3ccc4ccc5c(-c6ccc7ccccc7c6)ccc6ccc3c4c65)ccc2c1] H5
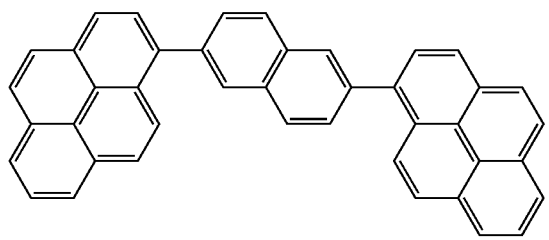 [SMILES: c1cc2ccc3ccc(-c4ccc5cc(-c6ccc7ccc8cccc9ccc6c7c89)ccc5c4)c4ccc(c1)c2c34] H6
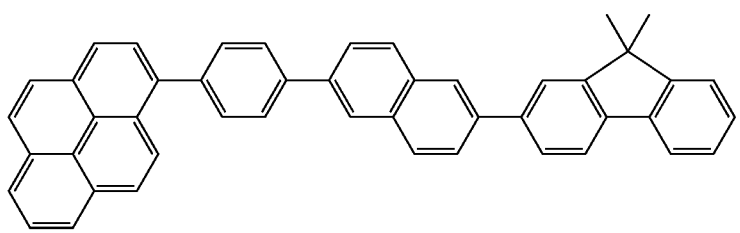 [SMILES: CC1(C)c2ccccc2-c2ccc(-c3ccc4cc(-c5ccc(-c6ccc7ccc8cccc9ccc6c7c89)cc5)ccc4c3)cc21] H7
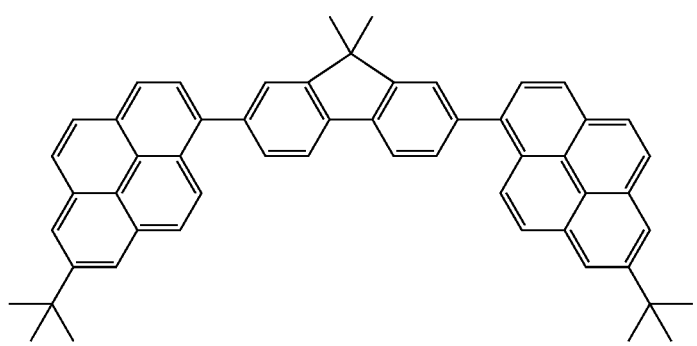 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] H8
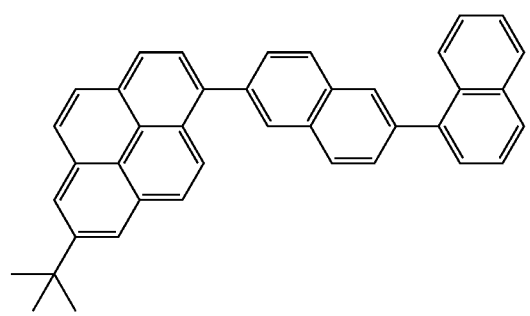 [SMILES: CC(C)(C)c1cc2ccc3ccc(-c4ccc5cc(-c6cccc7ccccc67)ccc5c4)c4ccc(c1)c2c34] H9

TABLE 2-continued
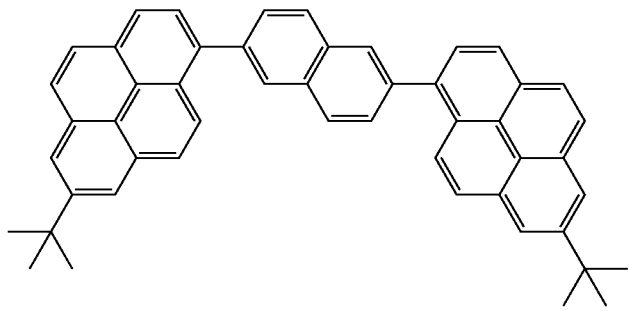 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34] H10
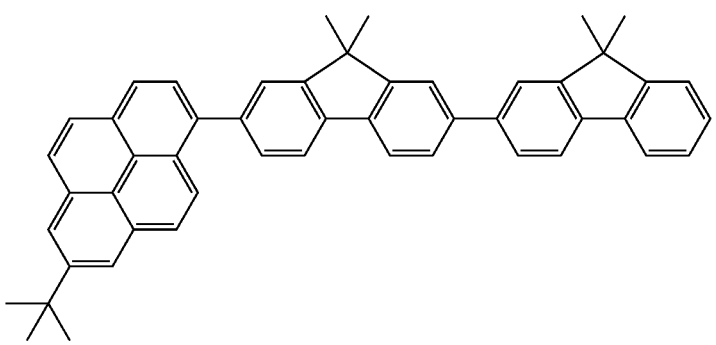 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34] H11
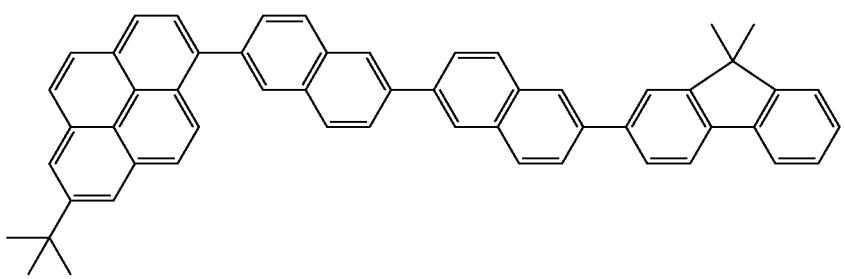 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34] H12
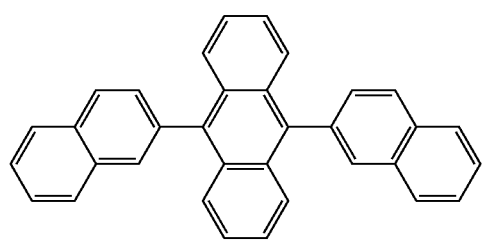 [SMILES: c1ccc2cc(-c3c4ccccc4c(-c4ccc5ccccc5c4)c4ccccc34)ccc2c1] H13
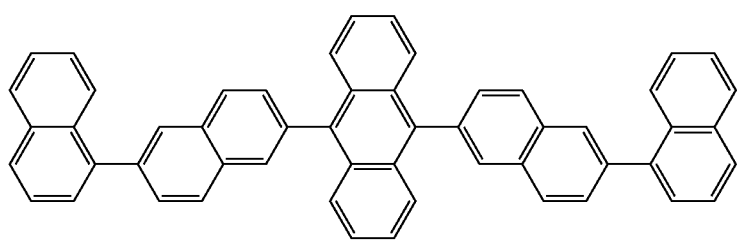 [SMILES: c1ccc2c(-c3ccc4cc(-c5c6ccccc6c(-c6ccc7cc(-c8cccc9ccccc89)ccc7c6)c6ccccc56)ccc4c3)cccc2c1] H14
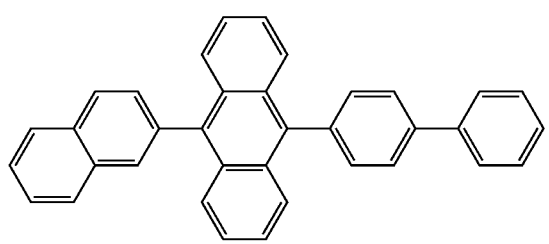 [SMILES: c1ccc(-c2ccc(-c3c4ccccc4c(-c4ccc5ccccc5c4)c4ccccc34)cc2)cc1] H15

TABLE 2-continued
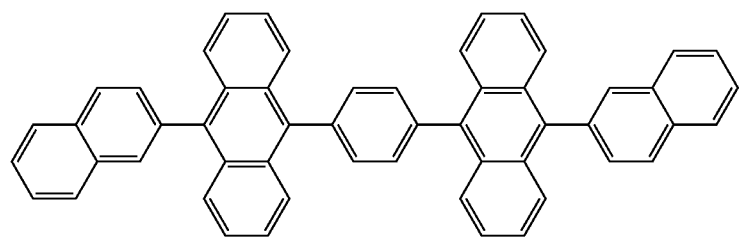 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H16
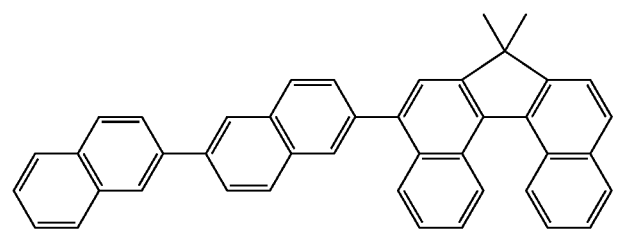 [SMILES: CC1(C)c2ccc3ccccc3c2-c2c1cc(-c1ccc3cc(-c4ccc5ccccc5c4)ccc3c1)c1ccccc21] H17
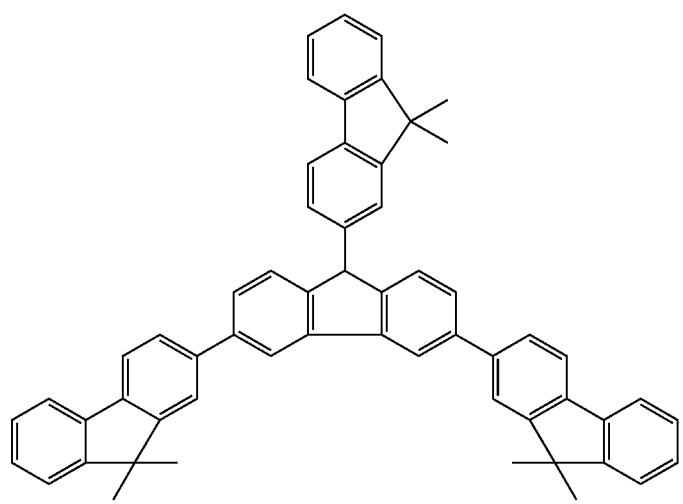 [SMILES: CC1(C)c2ccccc2-c2ccc(-c3ccc4c(c3)-c3cc(-c5ccc6c(c5)C(C)(C)c5ccccc5-6)ccc3C4c3ccc4c(c3)C(C)(C)c3ccccc3-4)cc21] H18
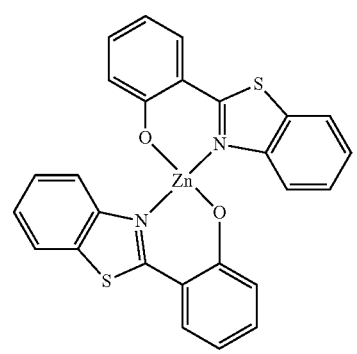 H19

TABLE 2-continued
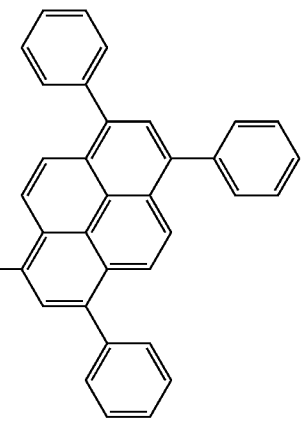 H20
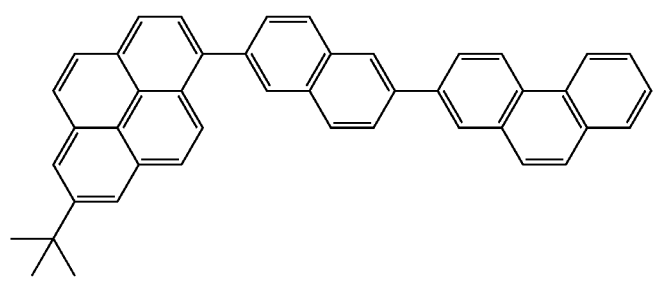 [SMILES: CC(C)(C)c1cc2ccc3ccc(-c4ccc5cc(-c6ccc7c(ccc8ccccc87)c6)ccc5c4)c4ccc(c1)c2c34] H21
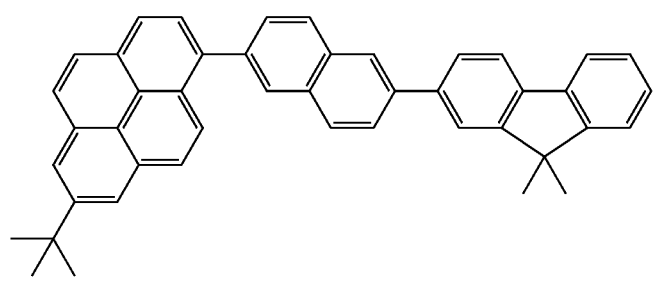 [SMILES: CC(C)(C)c1cc2ccc3ccc(-c4ccc5cc(-c6ccc7c(c6)C(C)(C)c6ccccc6-7)ccc5c4)c4ccc(c1)c2c34] H22
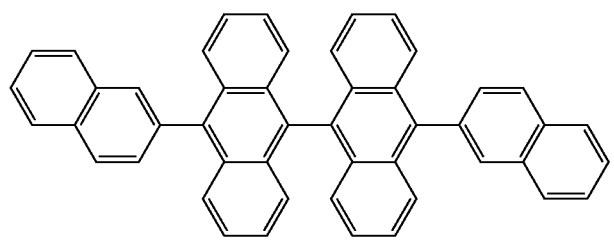 [SMILES: c1ccc2cc(-c3c4ccccc4c(-c4c5ccccc5c(-c5ccc6ccccc6c5)c5ccccc45)c4ccccc34)ccc2c1] H23
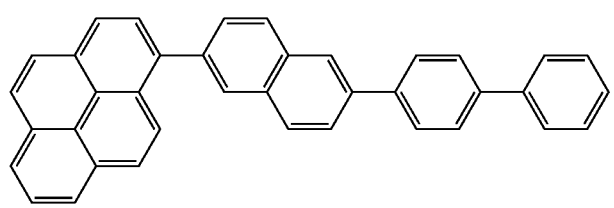 [SMILES: c1ccc(-c2ccc(-c3ccc4cc(-c5ccc6ccc7cccc8ccc5c6c78)ccc4c3)cc2)cc1] H24

TABLE 2-continued

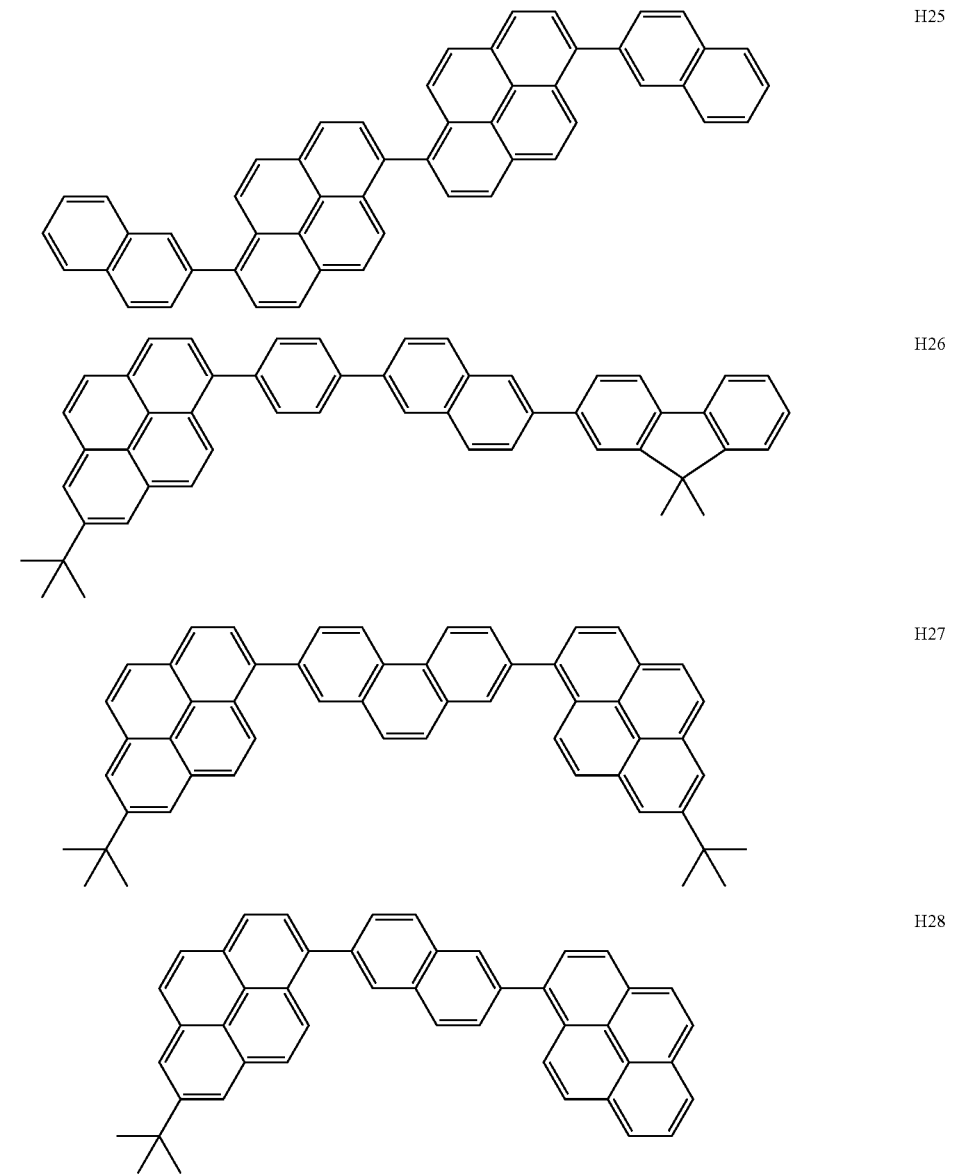

Other examples of the host compound include fused ring compounds (e.g., fluorene derivatives, naphthalene derivatives, anthracene derivatives, pyrene derivatives, carbazole derivatives, quinoxaline derivatives, and quinoline derivatives), organic aluminum complexes such as tris(8-quinolinolato)aluminum, organic zinc complexes, and polymer derivatives such as triphenylamine derivatives, poly(fluorene) derivatives, and poly(phenylene) derivatives. However, the present invention is not limited to these examples.

The electron injection compound and the electron transport compound are appropriately selected by considering, for example, the balance with the hole mobility of the hole injection compound and the hole transport compound. Examples of the compounds that have functions of injecting and transporting electrons include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

The constituent material of the anode can have a large work function. Examples thereof include single metals such as gold, platinum, silver, copper, nickel, palladium, cobalt, selenium, vanadium, and tungsten, alloys of two or more of these single metals, and metal oxides such as tin oxide, zinc oxide, indium oxide, indium tin oxide (ITO), and indium zinc oxide. Electrically conductive polymers such as polyaniline, polypyrrole, and polythiophene can also be used. These electrode substances may be used alone or in combination. The anode may be constituted by single layer or two or more layers.

In contrast, the material of the cathode can have a small work function. Examples of the cathode material include single metals such as alkali metals, e.g., lithium, alkaline earth metals, e.g., calcium, aluminum, titanium, manganese, silver, lead, and chromium. Alloys of two or more of these single metals can also be used. For example, magnesium-silver, aluminum-lithium, and aluminum-magnesium can be used. Metal oxides such as indium tin oxide (ITO) can also be used. These electrode substances may be used alone or in combination. The cathode may be constituted by single layer or two or more layers.

In the organic light-emitting device according to this embodiment, a layer that contains the organic compound of this embodiment and layers composed of other organic compounds are formed by the following method. Typically, thin films are formed by vacuum vapor deposition, ionized evaporation, sputtering, plasma, or a coating technique in which a material is dissolved in an appropriate solvent (e.g., spin-coating, dipping, casting, a Langmuir-Blodgett technique, and an ink jet technique). When layers are formed by vacuum vapor deposition or a solution coating technique, crystallization does not readily occur and stability overtime is improved. When a coating technique is used to form films, an appropriate binder resin may be used in combination to form films.

Examples of the binder resin include, but are not limited to, polyvinyl carbazole resins, polycarbonate resins, polyester resins, ABS resins, acrylic resins, polyimide resins, phenol resins, epoxy resins, silicone resins, and urea resins. These binder resins may be used alone as a homopolymer or in combination as a copolymer. If necessary, additives such as plasticizers, antioxidants, and UV absorbers may be used together.

The organic light-emitting device of this embodiment can be used in display apparatuses and lighting apparatuses. The organic light-emitting device can also be used as the exposure light source of an electrophotographic image-forming apparatus or a backlight of a liquid crystal display apparatus.

When the organic light-emitting device of this embodiment is used as a component of a display apparatus, the organic light-emitting device is installed in a display unit. The display unit includes plural pixels and the organic light-emitting device of this embodiment is installed in each pixel. The display apparatus can also be used as an image display apparatus of a personal computer or the like.

The display apparatus may be used in a display unit of an imaging apparatus such as a digital camera and a digital video camera. An imaging apparatus is an apparatus that includes a display unit and an imaging unit that includes an imaging optical system for capturing images.

An image display apparatus equipped with the organic light-emitting device of this embodiment will now be described.

FIG. 1 is a schematic cross-sectional view showing an example of an image display apparatus equipped with the organic light-emitting device of this embodiment.

An image display apparatus 1 shown in FIG. 1 includes a substrate 11 such as a glass substrate and a moisture-proof film 12 on the substrate 11. The moisture-proof film 12 protects a TFT or organic compound layers. A gate electrode 13 composed of chromium or the like is formed on the moisture-proof film 12. A gate insulating film 14 is formed over the gate electrode 13. A semiconductor layer 15 is formed over the gate insulating film 14.

A TFT element 18 includes the semiconductor layer 15, a drain electrode 16, and a source electrode 17. An insulating film 19 is provided on the top of the TFT element 18. The source electrode 17 is connected to an anode 111 of the organic light-emitting device through a contact hole (through hole) 110.

Although an organic compound layer 112 is illustrated as a single layer shown in FIG. 1, the organic compound layer 112 is actually a laminate constituted by two or more layers. In order to suppress deterioration of the organic light-emitting device, a first protective layer 114 and a second protective layer 115 are formed on a cathode 113.

The luminance of the emission from the organic light-emitting device is controlled by electric signals supplied from the TFT element 18. Since plural light-emitting devices are provided on the surface, an image can be displayed by controlling the emission luminance of the respective light-emitting devices.

When a display apparatus using the organic light-emitting devices of the embodiment is driven, high-quality images can be stably displayed over a long time.

EXAMPLES

The present invention will now be described by using non-limiting examples.

Example 1

Synthesis of example compound 1-1

Example compound 1-1 was synthesized through a process described below.
(1) Synthesis of 4,10-Diazachrysene
4,10-Diazachrysene was synthesized in accordance with a procedure described in NPL 1, pp. 88 to 89, "2.1. Materials".
(2) Synthesis of Intermediate Compound 1

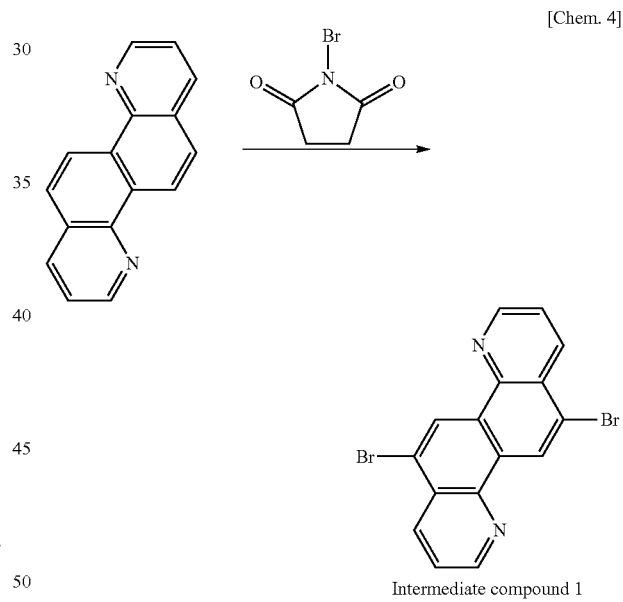

Intermediate compound 1

After 4,10-diazachrysene (3.00 g, 13.0 mmol) was dissolved in concentrated sulfuric acid (20 ml), N-bromosuccinimide (5.10 g, 28.7 mmol) was added to the resulting concentrated sulfuric acid solution. The reaction solution was then stirred for 2 hours under heating on a silicone oil bath heated to 70 degrees Celsius. After the reaction solution was cooled to room temperature, the reaction solution was slowly poured into 300 g of ice and the resulting yellow solution was neutralized with 28% ammonia water. Gray solids precipitated by the neutralization with ammonia water were filtered, washed with water and then methanol, and vacuum dried under heating at 80 degrees Celsius to obtain a crude product. The crude product was recrystallized with a chlorobenzene/methanol mixed solvent to obtain 4.14 g (yield: 82%) of an intermediate compound 1.

(3) Synthesis of Intermediate Compound 2

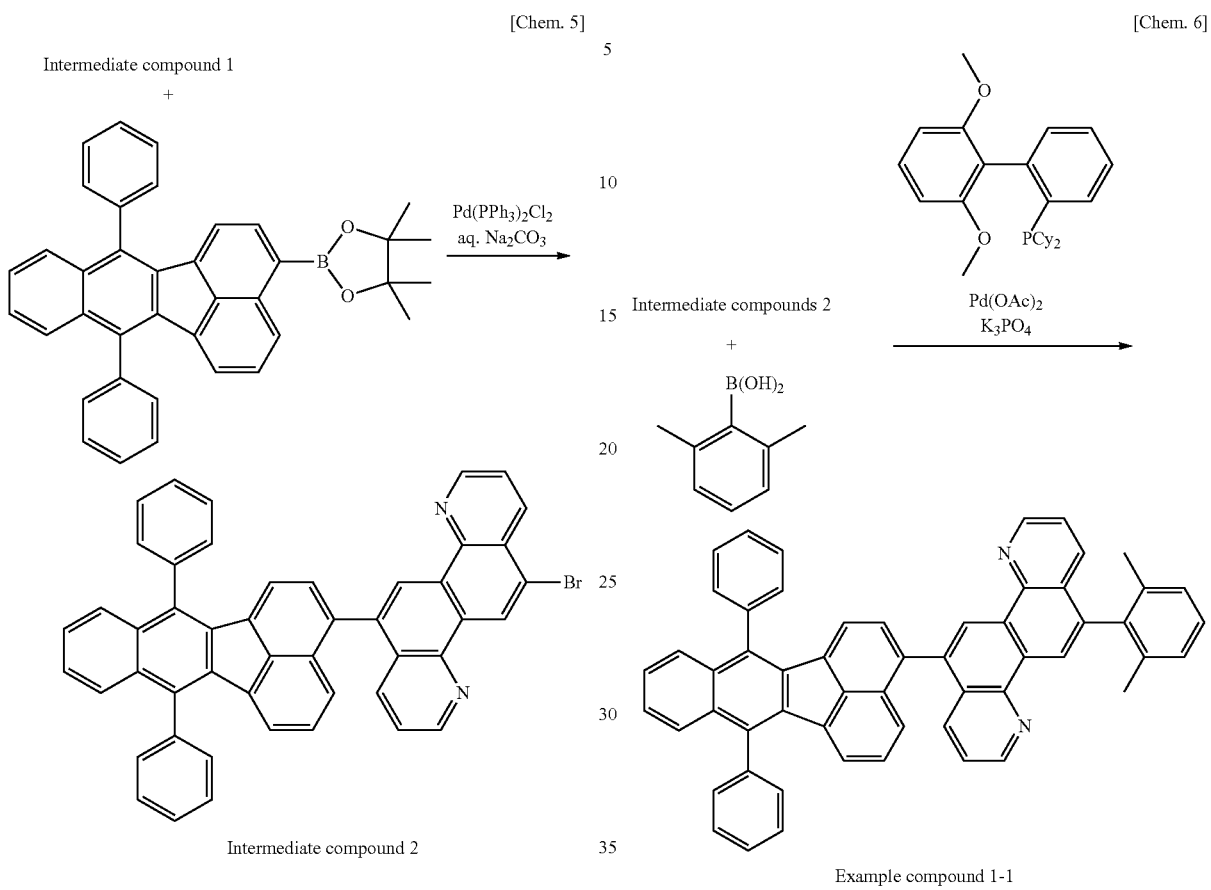

The following compounds are charged into a reactor in a nitrogen atmosphere. In charging, the compounds are heated and dissolved in a mixed solvent of toluene (100 ml) and ethanol (5 ml).

intermediate compound 1: 0.329 g (0.848 mmol)

2-(7,12-diphenylbenzo[k]fluoranthen-3-yl)-4,4,5,5-tetramethyl-1,3,2-dioxaborolane: 0.300 g (0.566 mmol)

Pd(PPh$_3$)$_2$Cl$_2$: 0.0397 g (0.0566 mmol)

To the reaction solution, an aqueous solution containing 0.120 g (1.13 mmol) sodium carbonate and 1 ml distilled water was added, and the reaction solution was stirred for 5 hours under heating on a silicone oil bath heated to 90 degrees Celsius. After the reaction solution was cooled to room temperature, water, toluene, and ethyl acetate were added and the solvent was extracted to obtain an organic layer. The water layer obtained by the first solvent extraction was further subjected to solvent extraction twice with a toluene-ethyl acetate mixed solvent. The obtained organic layer was added to the organic layer obtained in the first solvent extraction. The organic layer was washed with saturated saline and dried over sodium sulfate. The residue obtained by distilling away the solvent of the organic layer was purified by silica gel column chromatography (mobile phase: chloroform/heptane (3:2)). The purified product was vacuum dried at 100 degrees Celsius to obtain 0.245 g (yield: 61% on a pinacolboron basis) of an intermediate compound 2.

(4) Synthesis of Example Compound 1-1

The following compounds are charged into a reactor in a nitrogen atmosphere. The compounds charged here were suspended in toluene (5 ml) charged simultaneously.

intermediate compound 2: 0.210 g (0.295 mmol)
2,6-dimethylphenylboronic acid: 0.133 g (0.882 mmol)
2-dicyclohexylphosphino-2',6'-dimethoxybiphenyl: 0.0134 g (0.0326 mmol)
palladium acetate: 0.0033 g (0.0148 mmol)
potassium phosphate: 0.376 g (1.77 mmol)

The reaction solution was then stirred for 6 hours under heating on a silicone oil bath heated to 100 degrees Celsius. After the reaction solution was cooled to room temperature, water, toluene, and ethyl acetate were added and the solvent was extracted to obtain an organic layer. The water layer obtained by the first solvent extraction was further subjected to solvent extraction twice with a toluene-ethyl acetate mixed solvent. The obtained organic layer was added to the organic layer obtained in the first solvent extraction. The organic layer was washed with saturated saline and dried over sodium sulfate. The residue obtained by distilling away the solvent of the organic layer was purified by silica gel column chromatography (developing solvent: chloroform/heptane (2:1)). The purified product was vacuum dried at 120 degrees Celsius and purified by sublimation to obtain 0.139 g (yield: 64%) of example compound 1-1 as yellow solids.

Matrix-assisted laser desorption ionization-time of flight mass spectrometry (MALDI-TOF MS) was conducted to confirm 736.3, which is M$^+$ of this compound.

$^1$H-NMR measurement was conducted to confirm the structure of this compound.

$^1$H-NMR (CDCl$_3$, 600 MHz) δ (ppm): 9.51 (1H, s), 9.30 (1H, s), 9.01 (2H, m), 8.00 (1H, dd), 7.86 (1H, dd), 7.67-7.60 (12H, m), 7.53 (1H, d), 7.47-7.43 (3H, m), 7.38-7.30 (3H, m), 7.23 (2H, d), 7.18 (1H, t), 6.77 (1H, d), 6.63 (1H, d), 2.00 (6H, s)

The fluorescent spectrum of a toluene solution of example compound 1-1 (concentration: 1×10$^{-5}$ mol/l) was measured with F-4500 produced by Hitachi Ltd. The excitation wavelength was set to 370 nm. The measurement results showed that the fluorescence peak wavelength was 439 nm and the CIE chromaticity was (0.146, 0.099).

Example 2

An organic light-emitting device including an anode, a hole transport layer, an emission layer, an electron transport layer, an electron injection layer, and a cathode sequentially stacked on a substrate in that order was prepared by the following method.

A film of indium tin oxide (ITO) was formed on a glass substrate by sputtering to form an anode. The thickness of the anode was 120 nm. The substrate with the anode was ultrasonically washed with acetone and then isopropyl alcohol (IPA) and then washed with pure water, followed by drying. UV/ozone washing followed. The resulting processed substrate was used as a transparent electrically conductive supporting substrate.

Compound A indicated below serving as a hole transport material was mixed with chloroform to prepare a chloroform solution having a solute concentration of 0.1 wt %.

[Chem. 7]

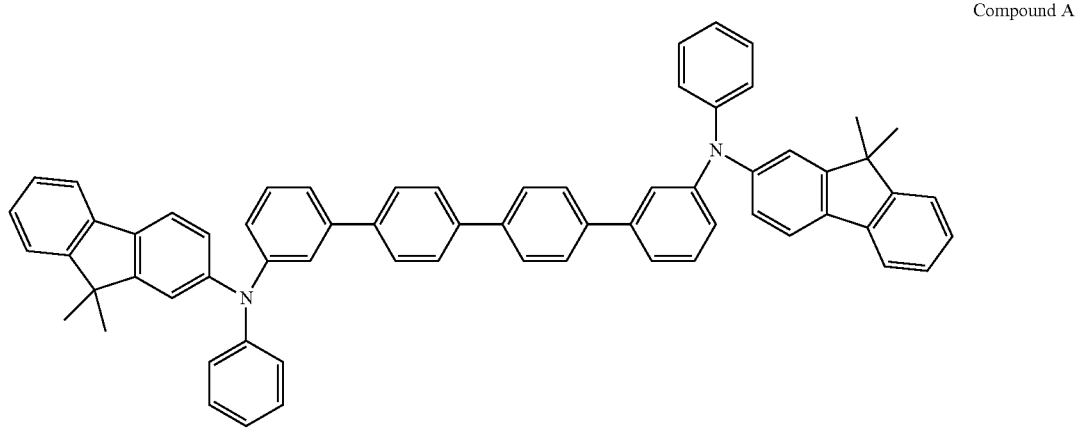

Compound A

The chloroform solution was dropped on the anode and spin-coating was conducted at 500 RPM for 10 seconds and then at 1000 RPM for 40 seconds to form a film. The thin film was dried under heating for 10 minutes in a vacuum oven at 80 degrees Celsius to completely remove the solvent in the thin film and to thereby form a hole transport layer. The thickness of the hole transport layer was 40 nm.

Next, example compound 1-1 and compound B indicated below were co-deposited on the hole transport layer to form an emission layer. The degree of vacuum during deposition was 1.0×10$^{-4}$ Pa and the deposition rate was set to 0.1 nm/sec or more and 0.2 nm/sec or less. The mixing ratio of example compound 1-1 to compound B in the emission layer was adjusted to 5:95 on a weight basis. The thickness of the emission layer was 30 nm.

[Chem. 8]

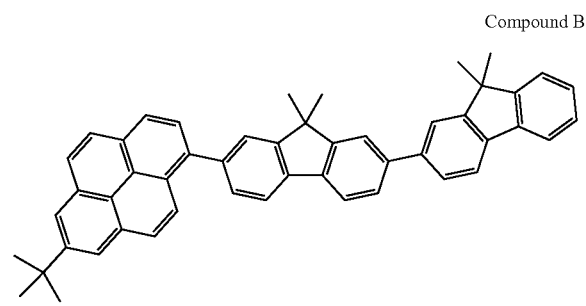

Compound B

Next, 2,9-bis[2-(9,9'-dimethylfluorenyl)]-1,10-phenanthroline was formed into film on the emission layer by vacuum vapor deposition. The thickness of the electron transport layer was set to 30 nm, the degree of vacuum during deposition was set to 1.0×10$^{-4}$ Pa, and the deposition rate was set to 0.1 nm/sec or more and 0.2 nm/sec or less.

A film of lithium fluoride (LiF) was formed on the electron transport layer by vacuum vapor deposition to form an electron injection layer. The thickness of the electron injection layer was set to 0.5 nm, the degree of vacuum during deposition was set to 1.0×10$^{-4}$ Pa, and the deposition rate was set to 0.01 nm/sec. Next, an aluminum film was formed on the electron injection layer by vacuum vapor deposition to form a cathode. The thickness of the cathode was set to 100 nm, the degree of vacuum during deposition was set to 1.0×10$^{-4}$ Pa, and the deposition rate was set to 0.5 nm/sec or more and 1.0 nm/sec or less.

Lastly, a protective glass plate was placed in a dry air atmosphere to prevent deterioration of the organic light-emitting device by adsorption of moisture, and the device was sealed with an acrylic resin adhesive. An organic light-emitting device was obtained as such.

The properties of the resulting organic light-emitting devices were measured and evaluated. In particular, the current-voltage characteristic was measured with a microammeter 4140B produced by Hewlett-Packard Co., and the emission luminance was measured with BM7 produced by TOPTON CORPORATION. As a result, excellent blue emission with an emission luminance of 352 cd/m² was observed under application of a voltage of 4.0 V. A voltage was applied to this device for 100 hours in a nitrogen atmosphere. Continuation of satisfactory emission was confirmed.

The present invention provides a heterocyclic compound that has an emission hue with extremely high purity, high-luminance optical output at high efficiency, and durability, and an organic light-emitting device including the heterocyclic compound.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-190634, filed Aug. 20, 2009, which is hereby incorporated by reference herein in its entirety.

The invention claimed is:

1. A heterocyclic compound that is used in organic light-emitting devices represented by general formula [1]:

[Chem. 1]

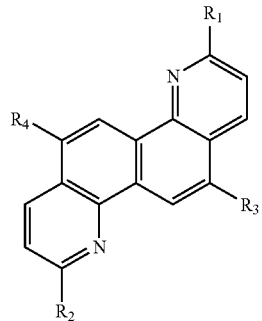

[1]

(where $R_1$ to $R_4$ each independently represent a hydrogen atom, a substituted or unsubstituted aryl group, or a substituted or unsubstituted heterocyclic group;
and at least one of $R_1$ to $R_4$ represents a substituted or unsubstituted fused polycyclic aromatic group having four or more rings or a substituted or unsubstituted fused polycyclic heterocyclic group having four or more rings.

2. The heterocyclic compound according to claim 1, wherein at least one of $R_1$ to $R_4$ represents a benzofluoranthenyl group.

* * * * *